United States Patent
Yilmaz et al.

(10) Patent No.: US 10,721,956 B2
(45) Date of Patent: Jul. 28, 2020

(54) VAPORISABLE MATERIAL PLUG AND CAPSULE

(71) Applicant: JT International SA, Geneva (CH)

(72) Inventors: Ugurhan Yilmaz, Konz (DE); Thomas Johaentges, Schweich (DE); Toshifumi Suzuki, Cologny (CH)

(73) Assignee: JT International SA (CH)

( * ) Notice: Subject to any disclaimer, the term of this patent is extended or adjusted under 35 U.S.C. 154(b) by 80 days.

(21) Appl. No.: 14/888,593

(22) PCT Filed: May 2, 2014

(86) PCT No.: PCT/EP2014/058982
§ 371 (c)(1),
(2) Date: Nov. 2, 2015

(87) PCT Pub. No.: WO2014/177687
PCT Pub. Date: Nov. 6, 2014

(65) Prior Publication Data
US 2016/0100624 A1    Apr. 14, 2016

(30) Foreign Application Priority Data
May 2, 2013 (EP) ..................................... 13166198

(51) Int. Cl.
*A24B 3/14* (2006.01)
*A24D 1/14* (2006.01)
(Continued)

(52) U.S. Cl.
CPC .............. *A24B 3/14* (2013.01); *A24B 15/186* (2013.01); *A24D 1/14* (2013.01); *A24F 47/004* (2013.01);
(Continued)

(58) Field of Classification Search
CPC ... A24D 1/14; A61M 15/0028; A61M 15/003; A61M 15/06; A24F 47/004;
(Continued)

(56) References Cited

U.S. PATENT DOCUMENTS 3,766,929 A    10/1973   Roman, Sr.
4,838,286 A *   6/1989   Phelpstead ............... A24D 1/00
                                                          131/360
(Continued)

FOREIGN PATENT DOCUMENTS

DE    3835948 A1    5/1989
GB    1340926 A *  12/1973   ............... A24D 1/00
(Continued)

OTHER PUBLICATIONS

Cussler, E. L., "Fundamentals of Mass Transfer", Published 2009, 3rd Edition, p. 211-212 (Year: 2009).*
(Continued)

*Primary Examiner* — Michael J Felton
*Assistant Examiner* — Sonny V Nguyen
(74) *Attorney, Agent, or Firm* — Lerner, David, Littenberg, Krumholz & Mentlik, LLP

(57) ABSTRACT

A plug (25) of vaporisable material for a vapour generating device (1) which generates a vapour by heating at least the base of the plug (25) is disclosed. The plug (25) comprises vaporisable material shaped such that it defines a cavity (26) within the vaporisable material.

17 Claims, 2 Drawing Sheets

Figure 1:
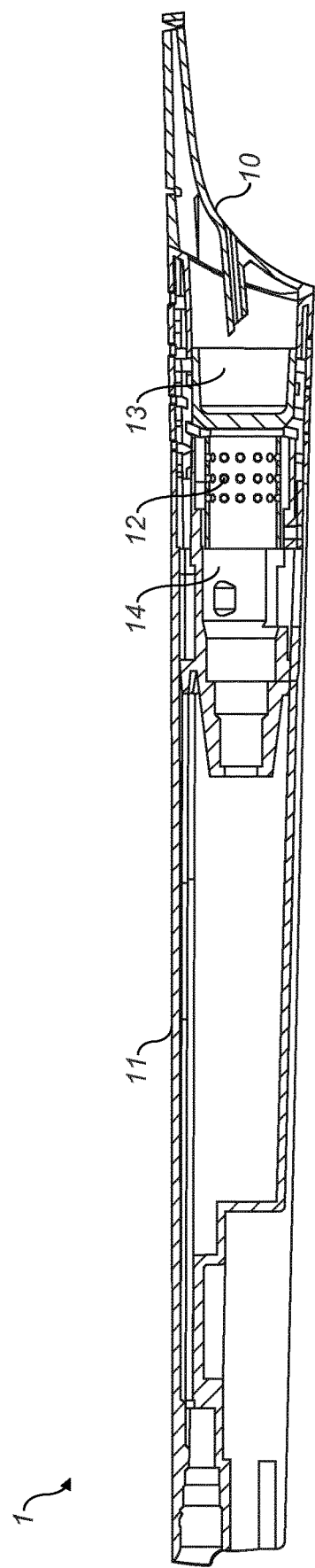

(51) Int. Cl.
*A24F 47/00* (2020.01)
*A61M 15/06* (2006.01)
*A61M 15/00* (2006.01)
*A24B 15/18* (2006.01)
*A61M 11/04* (2006.01)

(52) U.S. Cl.
CPC ........ *A61M 15/0028* (2013.01); *A61M 15/06* (2013.01); *A61M 11/047* (2014.02); *A61M 15/0036* (2014.02)

(58) Field of Classification Search
CPC ...... A24F 47/002; A24F 47/008; A24F 47/00; A24F 47/006; A24B 3/14; A24B 13/00; A24B 13/02
USPC .......................................... 131/111, 366, 348
See application file for complete search history.

(56) References Cited

U.S. PATENT DOCUMENTS

| | | | |
|---|---|---|---|
| 4,924,886 A | | 5/1990 | Litzinger |
| 4,944,317 A | * | 7/1990 | Thal .......................... A24D 1/14 131/348 |
| 5,144,962 A | * | 9/1992 | Counts ................... A24F 47/008 131/194 |
| 2005/0066985 A1 | * | 3/2005 | Borschke ............... A24F 47/004 131/360 |
| 2007/0186944 A1 | * | 8/2007 | Strickland .............. A24B 13/00 131/361 |
| 2007/0283972 A1 | * | 12/2007 | Monsees ................ A24F 47/006 131/273 |
| 2008/0132830 A1 | * | 6/2008 | Hague ..................... A61J 7/003 604/36 |
| 2009/0151717 A1 | * | 6/2009 | Bowen ................. A61M 11/041 128/200.23 |
| 2014/0166029 A1 | * | 6/2014 | Weigensberg ........ A24F 47/008 131/329 |

FOREIGN PATENT DOCUMENTS

| | | |
|---|---|---|
| GB | 2469850 A | 11/2010 |
| GB | 2473264 A | 3/2011 |
| WO | 2007012007 A2 | 1/2007 |
| WO | 2009079641 A2 | 6/2009 |
| WO | 2013120854 A1 | 8/2013 |

OTHER PUBLICATIONS

International Search Report for Application No. PCT/EP2014/058982 dated Aug. 12, 2014.
International Written Opinion for Application No. PCT/EP2014/058982 dated Aug. 12, 2014.

* cited by examiner

VAPORISABLE MATERIAL PLUG AND CAPSULE

CROSS REFERENCE TO RELATED APPLICATIONS

The present application is a national phase entry under 35 U.S.C. § 371 of International Application No. PCT/EP2014/058982, filed May 2, 2014, which claims priority to European Patent Application No. 13166198.5, filed May 2, 2013, the disclosures of which are incorporated herein by reference.

The present invention relates to a plug of vaporisable material and a vaporisable material-containing capsule for use in a vapour generating device. Devices which heat rather than burn vaporisable material, such as tobacco, to create a vapour for inhalation are becoming popular. They generally comprise a heat source powered by gas or electricity and a chamber for receiving a plug of vaporisable material or a disposable capsule containing a vapour-generating product. In use the plug or capsule is inserted into the device and heated by the heat source to generate a vapour for inhalation. An example of such a device can be found in PCT publication WO 2009/079641.

Such devices have become popular because they can provide a user with an experience very similar to smoking the vaporisable material but without the burning of plant material such as tobacco.

However, such devices are not always popular with consumers because they can produce inconsistent levels of vapour and are often unreliable in terms of the length of use of an individual capsule, leaving to an inconsistency of flavour delivery to a user.

The present invention seeks to provide a plug of vaporisable material and capsule for containing such a plug which overcomes at least some of these problems.

According to the present invention there is provided a plug of vaporisable material for a vapour generating device which generates a vapour by heating at least the base of the plug, the plug comprising:

vaporisable material shaped such that it defines a cavity within the vaporisable material, the cavity being frusto-conical in shape.

The plug may be provided in a capsule.

With a plug or capsule with contents comprising a plug in the manner defined it is possible to provide accurate and consistent filling of the capsule with product. Furthermore, by defining the thickness of the material within the plug, by provision of the cavity within the contents, when the plug or a capsule containing such a plug is heated in use it is possible to define quite specifically the speed of release of vapour to a user and the length of time over which vapour is released. Also, by provision of the cavity it is possible to reduce significantly the draw resistance experienced by the user when drawing on vapour produced by the material.

The frusto-conical shape improves significantly the consistency of flavour delivery and greatly improves a user's experience when using the heating device. The angle of inclination of the frusto-conical shape with respect to a line perpendicular to the base of the plug or capsule may be in the range of 10 to 15 degrees and may be about 12 degrees.

It will be appreciated that the thickness of the contents between the base of the plug and the cavity can be controlled to optimise vapour generation and draw characteristics and may vary dependent on the overall depth of the plug, the material contents and the volume of material. The thickness may be controlled so that the ratio of overall plug depth to thickness of material between the base and the cavity is in the range of thirteen to one and four to one. In one embodiment the cavity may be formed so that the thickness of the contents between the cavity and the base of the plug or capsule is in the range of 1.5 mm +/−0.5 mm.

The material in the plug may comprise tobacco.

Figure 2:
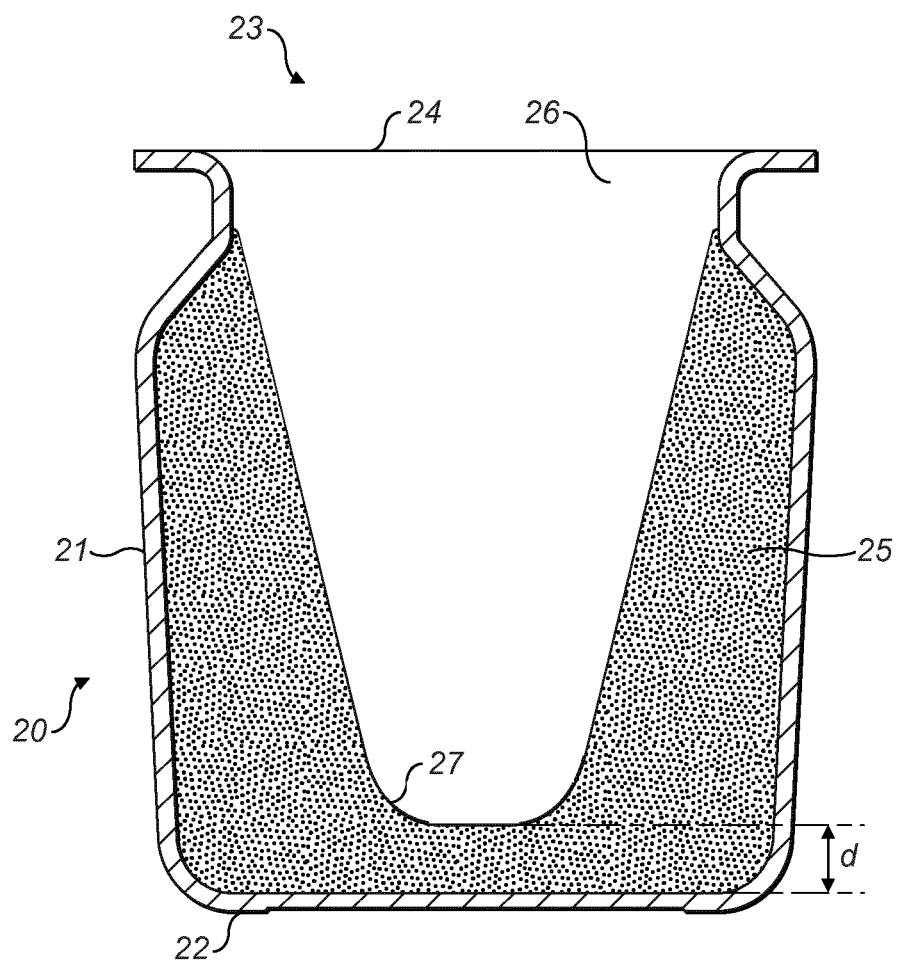

One example of the present invention will now be described with reference to the accompanying drawings in which:

FIG. 1 is a side cross-sectional schematic view of a heating device comprising a capsule according to the present invention; and FIG. 2 is a side cross-sectional view through a plug and capsule in accordance with the invention.

Referring to FIG. 1 there is shown a tobacco heating device 1 of the type generally described in PCT publication WO 2009/079641. The device has a mouthpiece 10, body 11, heater 12, heating chamber 13 and a fuel supply 14. The device also usually has control components to regulate the temperature of the device particularly within the heating chamber to control a container 20 placed within the device in use. Whilst this example device uses a combustible fuel as a heat source, it will be appreciated that the device may have another type of heat source and power supply, such as an electrical heater and battery, for example.

In use a capsule 20 is inserted into the heating chamber 13, and the heater 12 supplied with fuel from the fuel tank 14 to heat the heating chamber 13, under the control of a user. The contents of the capsule 20 are heated by the heater 12 to create an aerosol vapour based on the contents of the container, that aerosol then being inhaled by the user via the mouth piece 10.

Referring to FIG. 2, a plug of vaporisable material 25 according to the invention is shown. In this example the plug is provided in a capsule 20. It is possible to provide the plug in a user-removable wrapper which is taken off prior to insertion of the plug 25 into the heating chamber 13 of the device 1 or to supply the plug 25 in a dispenser which inserts the plug 25 into the device 1 to avoid handling by a user.

The capsule 20 comprises an outer body 21 with a base 22 and opening 23. Preferably the capsule body is made of a metal, crystalline or noncrystalline inorganic ceramic or plastic material capable of upholding temperatures of at least 180° C. A preferred material for the capsule according to the invention may be aluminium.

The opening 23 is sealed with a foil 24 to retain the plug of material 25 within the capsule 20 during transport and insertion into the device of FIG. 1 and to maintain the freshness of the product prior to use. Foil 24 is pierced by the device 1 upon insertion so that, when the plug of material 25 is heated in use through the capsule 20, the vapour which is generated can pass out of the capsule 20 and through the mouth piece 10. The material from which the plug 25 is formed is vaporisable under heating and may be a tobacco-based product which can have a number of compositions. Examples of the types of material are described in WO 2009/079641. The nature of the composition will depend upon a desired flavour to be provided to a user, as well as other factors such as intended storage lifetime.

It will be noted that the plug of material 25 within the capsule 20 is shaped and positioned within the capsule 20 such that it defines a central cavity 26 within the capsule 20 even when it is filled. It will be noted that the cavity 26 is generally frusto-conical in shape, with the apex 27 of the cavity being at the end closest the base 22 of the body 21 of the capsule 20 when in position. The cavity is formed by compressing the plug material with an appropriately shaped tool. If the plug is to be supplied in the capsule 20 this may be done either before or after the insertion of the plug 25 into the capsule 20 and before the foil seal 24 is applied. By providing such a cavity it is possible to control with accuracy and consistency the thickness d between the cavity 26 and the base 22 of the capsule 20.

The provision of a frusto-conical shape has further advantages in that it is possible to control, again with accuracy and consistency, the amount of plug material at any particular distance from the base of the plug.

What the applicant has appreciated is that by controlling the distribution of the contents of the plug of vaporisable material 25 with respect to their distance from the base of the plug it is possible to predetermine the heat profile of the contents with respect to time when the plug 25 is heated in use. This in turn ensures that the delivery of vapour, and hence flavour, to a user can also be predetermined with a significant degree of consistency and accuracy. By determining the thickness d of material at the base of the plug (which is where heat is applied), it is possible to predetermine the amount of vapour released on initial heating to control the amount of flavour released to a user. It has been determined that a thickness d in the range of 1.5 mm plus or minus 0.5 mm is particularly beneficial in ensuring speedy vapour generation after the start of heating. That is in the example shown in FIG. 2, a relative ratio of depth to thickness that lies in the range of approximately thirteen to one to four to one.

By controlling the angle of inclination of the frusto-conical cavity it is also possible to control the release of vapour as the capsule heats up over time from the base upwards thereby controlling the profile of vapour delivery over the total heating lifetime of the plug 25 to accurately predetermine the overall time of delivery of the entire contents of the plug in vapour form. This provides a user with a reliable and consistent experience in using the device. In this respect an angle of inclination for the inclined side of the frusto-conical shape in the range of 10 to 15 degrees from a line perpendicular to the base 22 of the capsule 20 has been found to be beneficial and an angle of 12 degrees from such a line is particularly beneficial.

As will be appreciated providing a cavity of frusto-conical shape it is possible to provide a relatively linear heat profile for the plug material with respect to time, which in turn provides a linear vapour delivery. It should also be noted that the plug of vaporisable material could be inserted straight into an oven of a device without being first introduced in a capsule. Having the plug introduced in a capsule helps the users to remove a used plug in a hygienic manner and avoids contamination of a clean plug by residues left in the oven by a prior plug.

The invention claimed is:

1. A plug of a vaporisable material for a vapour generating device which generates a vapour by heating at least a base of the plug, the plug comprising:
   the vaporisable material shaped such that it defines a cavity within the vaporisable material, wherein the cavity is frusto-conical in shape with an apex defined as a flat surface adjacent to the base of the plug, and an inclined side of the cavity of the vaporisable material is exposed,
   wherein the cavity is positioned such that there is a predetermined thickness of the vaporisable material between the apex of the cavity and the base of the plug, and
   wherein an angle of inclination of the inclined side of the frusto-conical cavity is in the range of 10 to 15 degrees with respect to a line perpendicular to the base of the plug.

2. The plug of claim 1, wherein the predetermined thickness of the vaporisable material is 1.5 mm+/−0.5 mm.

3. The plug of claim 1, wherein the cavity is shaped such that a cross-sectional area of the cavity substantially parallel to the base increases as the distance within the cavity to the base increases.

4. The plug of claim 3, wherein the increase in the cross-sectional area in the cavity is non-linear in relation to the distance to the base.

5. The plug of claim 4, wherein a ratio of overall plug depth to the predetermined thickness of the vaporisable material between the apex of the cavity and the base of the plug is in the range of thirteen to one and four to one.

6. The plug of claim 1, wherein the angle of inclination of the inclined side of the frusto-conical cavity is around 12 degrees with respect to the line perpendicular to the base of the plug.

7. The plug of claim 6, wherein the vaporisable material comprises tobacco.

8. A capsule containing a plug of the vaporisable material according to claim 7.

9. A capsule comprising:
   an outer body having a base; and
   the plug of the vaporisable material according to claim 1 contained within the base of the outer body.

10. The capsule of claim 9, wherein the cavity is unfilled such that it is exposed to air.

11. The capsule of claim 9, further comprising a user-removable wrapper in which the outer body and the plug are disposed.

12. The capsule of claim 9, wherein an opening of the outer body is sealed.

13. The capsule of claim 9, wherein an opening of the outer body is sealed with a foil.

14. The capsule of claim 13, wherein an entire surface of the cavity of the vaporisable material is uncovered and separated from the foil.

15. The capsule of claim 9, wherein the outer body is comprised of aluminium.

16. A kit comprising:
   a removable capsule according to claim 9; and
   a vapour generating device which generates a vapour by heating at least the base of the plug,
   wherein the removable capsule is insertable into a heating chamber of the vapour generating device.

17. A dispenser comprising:
   a plurality of the plugs of claim 1 to be inserted into a vapour generating device.

* * * * *